US008108381B2

(12) United States Patent
Eberholst et al.

(10) Patent No.: US 8,108,381 B2
(45) Date of Patent: Jan. 31, 2012

(54) SYSTEM AND METHOD FOR ANALYZING ELECTRONIC DATA RECORDS

(75) Inventors: Frey Aagaard Eberholst, Risskov (DK); André Elisseeff, Basel (CH); Peter Lundkvist, Aarhus V (DK); Ulf H. Nielsen, Langnau am Albis (CH); Erich M. Ruetsche, Pfaeffikon (CH)

(73) Assignee: International Business Machines Corporation, Armonk, NY (US)

( * ) Notice: Subject to any disclaimer, the term of this patent is extended or adjusted under 35 U.S.C. 154(b) by 690 days.

(21) Appl. No.: 12/212,950

(22) Filed: Sep. 18, 2008

(65) Prior Publication Data

US 2009/0083231 A1 Mar. 26, 2009

(30) Foreign Application Priority Data

Sep. 21, 2007 (EP) .................................. 07116996

(51) Int. Cl.
*G06F 17/30* (2006.01)
(52) U.S. Cl. ....................................... 707/713; 707/928
(58) Field of Classification Search .................. 707/609, 707/705, 713, 802, 928; 706/14, 15, 46, 706/61
See application file for complete search history.

(56) References Cited

U.S. PATENT DOCUMENTS

2001/0041992 A1 11/2001 Lewis et al.
2007/0130206 A1* 6/2007 Zhou et al. ................. 707/104.1

FOREIGN PATENT DOCUMENTS

WO   WO 2006/130162   12/2006
WO   WO 2006/133050   12/2006

OTHER PUBLICATIONS

Pedersen et al., Measures of Semantic Similarity and Relatedness in the Medical Domain, University of Minnesota May 2005, pp. 1-9.*
Lin, et al., "A Document Clustering and Ranking System for Exploring Medline Citations", Journal of the American Medical Informatics Assoc., vol. 14, No. 5, Sep. 1, 2007.
Alani, "TGVizTab: An Ontology Visualisation Extension for Protege", Internet Citation, URL: http://eprints.ecs.soton.ac.uk/8326/01, Retrieved Jul. 28, 2006.
Gosselin, et al. "Feature-based approach to semi-supervised similarity learning", Pattern Recognition, Elsevier, GB, vol. 39, No. 10, Oct. 1, 2006.

* cited by examiner

*Primary Examiner* — Fred I Ehichioya
(74) *Attorney, Agent, or Firm* — Vazken Alexanian

(57) ABSTRACT

A system and method for analyzing electronic data records including an annotation unit being operable to receive a set of electronic data records and to compute concept vectors for the set of electronic data records, wherein the coordinates of the concept vectors represent scores of the concepts in the respective electronic data record and wherein the concepts are part of an ontology, a similarity network unit being operable to compute a similarity network by means of the concept vectors and by at least one relationship between the concepts of the ontology, the similarity network representing similarities between the electronic data records, wherein the vertices of the similarity network represent the electronic data records and the edges of the similarity network represent similarity values indicating a degree of similarity between the vertices and steps for executing the system.

21 Claims, 12 Drawing Sheets

SYSTEM AND METHOD FOR ANALYZING ELECTRONIC DATA RECORDS

CROSS-REFERENCE TO RELATED APPLICATION

This application claims priority under 35 U.S.C. §119 to European Patent Application No. 07116996.5 filed Sep. 21, 2007, the entire contents of which are incorporated by reference herein.

BACKGROUND OF THE INVENTION

1. Field of the Invention

The present invention generally relates to a system for analyzing electronic data records. More particularly, the present invention relates to a method of analyzing electronic data records and a corresponding computer program.

2. Description of the Related Art

With the advent of the internet and the openness of information systems, data sources have increased demand for new solutions on inter-operability and data exchange. New data sources are encoded into a variety of new formats requiring developers to continuously update their applications to maintain compatibility. Terminology standards such as Health Level 7 and SNOMED CT in the Healthcare industry have been defined to tackle this issue by providing a common language.

A particular challenge is data entry and data access. It is not feasible for a medical staff to follow some standards with, for instance, more than 300,000 terms such as SNOMED CT. Nurses and physicians usually do not have enough time to spend following some rules and learning a complex language while their patients are waiting for their support.

The use of terminology standards demands for tools to seamlessly manage unstructured data such as non-standardized electronic data and natural language.

In the field of healthcare, US 2001/0041992 A1 describes a system for accessing healthcare information using an anatomic user interface. The user has to enter healthcare information manually by annotating and clicking on the anatomic model.

Geographic Information Systems (GIS) such as Google™earth return annotations of geographical data manually entered by the user or system providers.

It is an object of the present invention to provide other solutions for analyzing electronic data records. It is a further object of the present invention to provide solutions for analyzing data records with enhanced search capabilities. It is a further object of the present invention to provide solutions that allow for automated annotation of graphical objects. It is a further object of the present invention to provide solutions for analyzing data records with improved user interfaces. It is a further object of the present invention to provide an improved system, an improved method and an improved computer program embodying solutions for analyzing electronic data records.

SUMMARY OF THE INVENTION

The present invention provides a system for analyzing electronic data records, which includes:

an annotation unit operable to receive a set of electronic data records and to compute concept vectors for the set of electronic data records, wherein the coordinates of the concept vectors represent scores of the concepts in the respective electronic data record and wherein the concepts are part of an ontology; and a similarity network unit operable to compute a similarity network by means of the concept vectors and by at least one relationship between the concepts of the ontology, the similarity network representing similarities between the electronic data records wherein the vertices of the similarity network represent the electronic data records and the edges of the similarity network representing similarity values indicating the degree of similarity between the vertices.

The preset invention further provides a method for analyzing electronic data records, which includes the steps of:

receiving a set of electronic data records;

computing concept vectors for the set of electronic data records, wherein the coordinates of the concept vectors represent scores of the concepts in the respective electronic data record and wherein the concepts are part of an ontology;

computing a similarity network by means of the concept vectors and by at least one relationship between the concepts of the ontology, the similarity network representing similarities between the electronic data records, wherein the vertices of the similarity network represent the electronic data records and the edges of the similarity network represent similarity values indicating a degree of similarity between the vertices; and performing predefined algorithms over the similarity network.

The present invention further provides a computer program product having computer usable program code configured to carry out instructions for analyzing electronic data records by a method including the steps of:

receiving a set of electronic data records;

computing concept vectors for the set of electronic data records, wherein the coordinates of the concept vectors represent scores of the concepts in the respective electronic data record and wherein the concepts are part of an ontology;

computing a similarity network by means of the concept vectors and by at least one relationship between the concepts of the ontology, the similarity network representing similarities between the electronic data records, wherein the vertices of the similarity network represent the electronic data records and the edges of the similarity network represent similarity values indicating a degree of similarity between the vertices; and performing predefined algorithms over the similarity network.

DETAILED DESCRIPTION OF THE PREFERRED EMBODIMENTS

Figure 1:
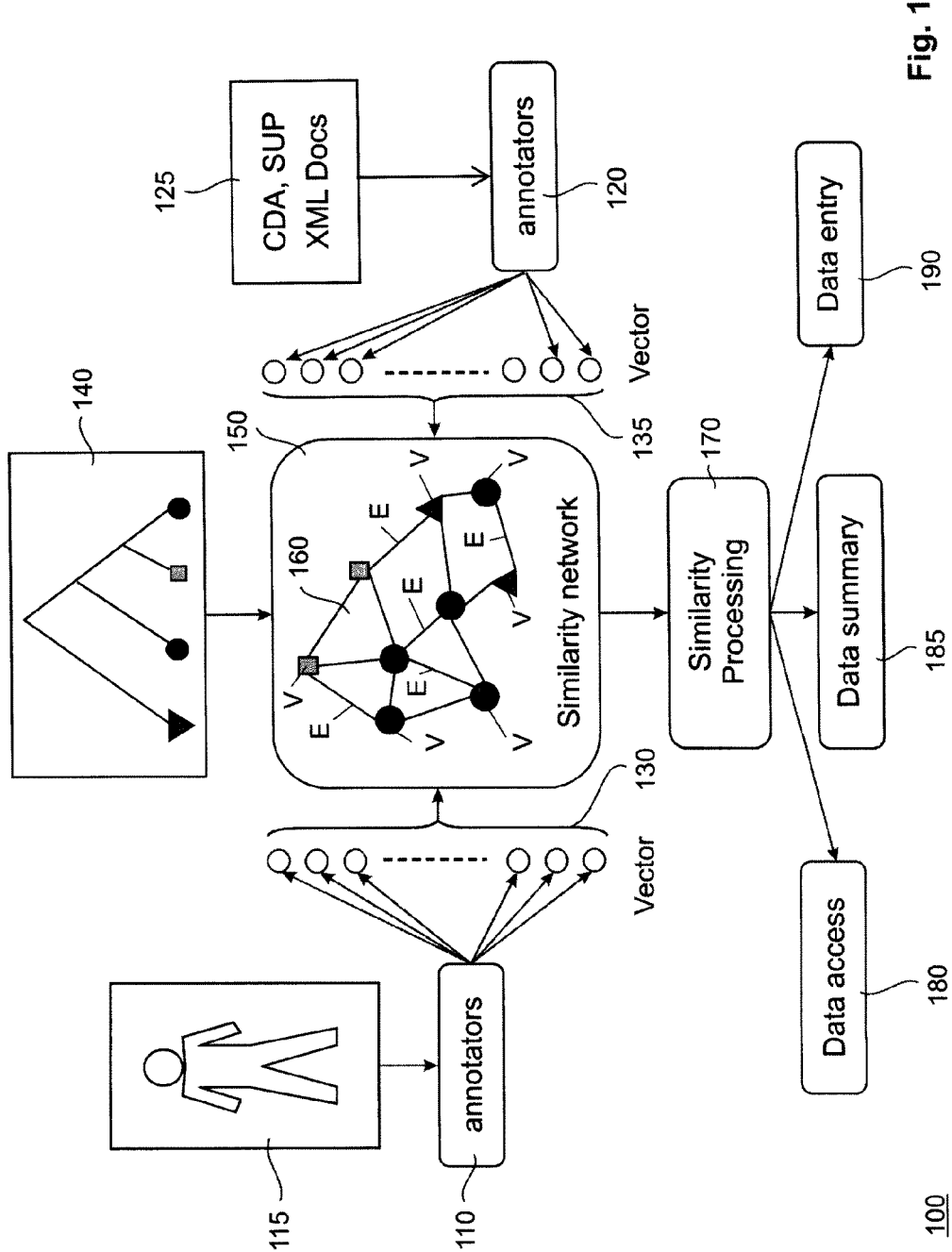
FIG. 1 shows a schematic illustration of a system for analyzing electronic data records according to an embodiment of the invention.

An ontology is understood as a specification of a conceptualization. It may be defined as a controlled or predefined vocabulary that describes objects and the relations between the objects in a formal way. The controlled or predefined vocabulary includes terms or words that describe the objects. The terms or words of the controlled vocabulary that describe the objects are denoted as concepts.

A concept preferably defines the meaning of a term and preferably relates to the semantics of the text rather than to its syntactic form. Many words can therefore relate to the same concept. The concept of Myocardial infarction (disorder) can be described for instance as myocardial infarction, cardiac infarction, heart attack, or infarction of heart. On the other hand, written words without contextual information are in general not enough to retrieve the concept. Hematoma, for instance, can be understood as a morphologic abnormality observed by a pathologist or can be considered as a diagnosis from a general practitioner.

The annotation unit uses the concepts of the ontology to compute concepts vectors for electronic data records. The coordinates of the concept vectors represent the scores of the concepts of the respective electronic data record. The scores are values that indicate the relevance of the respective concept for the respective electronic data record according to a predefined measure. Such measure may be, for example, a probability, that is, any number in (0, 1) or the term frequency-inverse document frequency (TF-DIF), which is a standardized measure in information retrieval.

As a result of the annotation, the electronic data records have been characterized in a formal way by means of the concept vectors.

The similarity network unit is operable to compute a similarity network for the electronic data records. Such a similarity network represents the similarities between the electronic data records and may be, for example, illustrated by means of a similarity graph. The similarity network includes vertices, which represent the electronic data records, and edges that couple pairs of vertices. The edges of the similarity network represent similarity values indicating the degree of similarity between the respective pair of vertices.

The similarity network unit utilizes as input the concept vectors and at least one relationship of the ontology. Such a relationship, also denoted as an attribute, may describe any kind of relation between the concepts of the ontology. Examples of relationships are the "is a," the "part of" and the "caused by" relationship.

The system according to this aspect of the invention allows for analyzing a set of electronic data records in an enhanced, structured, flexible and automated way. This facilitates multiple advantageous applications of the similarity network. By taking into account at least one relationship of the concepts of the ontology, hidden or non-obvious similarities between the electronic documents can be identified and detected.

By limiting the analysis to the set of electronic data records received by the annotation unit, advanced analysis of the set of electronic data records becomes feasible. This is particularly useful for applications in which only a limited set of electronic data records shall be analyzed in an advanced way.

The similarity network unit may use a predefined algorithm, function or method for computing the similarity values of the edges of the similarity network.

The predefined algorithm may be any algorithm that allows for computing similarities between the electronic data records that fulfill predefined similarity criteria.

According to an embodiment of this aspect of the invention, the similarity network unit uses a kernel-based algorithm for computing the similarity values.

A kernel based algorithm is an algorithm that bases its calculations over a set of inputs $(d_1, \ldots, d_m) \subset X^m$ using kernels. The input space X can correspond, for instance, to a set of strings, a set of graphs, a set of images or a set of real valued vectors. The kernels are defined as functions from X×X onto R such that, for any sequence of real numbers $(a_1, \ldots, a_m)$, the following formula holds true:

$$\sum_{i,j=1}^{m} a_i a_j k(d_i, d_j) \geq 0$$

In general, a kernel can be used as a measure of similarity between two inputs.

According to an embodiment of this aspect of the invention, the system includes a similarity processing unit operable to receive the similarity network as input and to perform predefined algorithms over the similarity network.

This allows for analyzing and comparing the electronic data records and to detect similarities between the electronic data records, in particular similarities based on one or more relationships of the ontology. The predefined algorithm may be in particular a similarity-based algorithm. A similarity-based algorithm is understood as an algorithm that uses the similarity values of the edges for computing properties or characteristics of the similarity network. This may involve searches over the similarity network with respect to a query or a summary of the most frequent concepts appearing in a sub-part of the similarity network. As an example, a similarity based algorithm may be a graph-based information retrieval technique such as manifold ranking. This allows for computing similarities between remote vertices, that is, vertices that are not directly connected by an edge.

Using the similarity network and similarity-based algorithms allows for performing data analysis by focusing on similarities between the electronic data records rather than on a standardized representation of the electronic data records. This is more robust with respect to potential errors during translation. By using the semantic structure encoded into the ontology, the comparison of data coming from different modalities is feasible. As an example, a graphical representation of a hand can be encoded as a SNOMED term corresponding to a "hand (anatomy)." A text mentioning the word "hand" will also be represented by the SNOMED term "hand," which is semantically close to "hand (anatomy)." Therefore, both electronic data records, although from different modalities, will be considered as similar.

According to an embodiment of this aspect of the invention, the similarity processing unit is operable to receive a query, including at least one vertex of the similarity network, and computing vertices of the similarity network that are similar to the query according to a predefined similarity criteria.

This allows for advanced searching applications. For example, the query might be issued by a user of the system and received via a user interface.

According to an embodiment of this aspect of the invention, the system is operable to analyze a first set of electronic data records and a second set of electronic data records, wherein the first set of electronic data records is a set of graphical electronic data records and the second set of electronic data records is a set of arbitrary electronic data records, wherein the similarity processing unit is operable to compute similarities between the first set of electronic data records and the second set of electronic data records.

The system according to this aspect of the invention can compute similarities between graphical electronic data records and arbitrary electronic data records. The graphical electronic data records may include any kind of graphical data of a graphical object. The arbitrary electronic data records may be any kind of data records that can be annotated, in particular textual data records. Computing similarities between graphical data records and arbitrary data records can be used, for example, for applications of graphical user interfaces.

According to a further embodiment of this aspect of the invention, the first set of electronic data records, that is, the set of graphical electronic data records, relates to a virtual model of an object. The object is a root concept of the ontology. Parts of the object can be described with further concepts of the ontology and can be characterized by means of concept vectors. This results in a structured representation of the graphical object. The second set of electronic data records may represent data records of an individual of the root concept. An individual of the root concept is the basic, that is, bottom level, component of the ontology. According to a further embodiment of this aspect of the invention, the object is a virtual model of a human body and the individuals are human patients. As a further example, the object could be a virtual model of a car and the individual an individual car.

According to a further embodiment of this aspect of the invention, the system includes an ontology database for storing data of the ontology, a graphical object database for storing graphical electronic data records of an object and a database for storing electronic data folders, wherein each data folder includes data records of an individual of the ontology.

As an example, in the healthcare domain the ontology database could store data of a healthcare ontology such as SNOMED. The graphical object database could store graphical data of a virtual human body.

The database for storing electronic data folders could have electronic data folders for each patient. These electronic data folders could store electronic medical records (EMR) of the respective patient.

According to a further embodiment of this aspect of the invention, the system includes a user interface for presenting a graphical representation of the first set of electronic data records, wherein the user interface includes a navigation function for navigating over the graphical representation of the first set of electronic data records and a selection function for selecting parts of the graphical representation of the first set of electronic data records.

According to a further embodiment of this aspect of the invention, the first set of electronic data records relates to a virtual model of a human body or a virtual model of an animal body and wherein the second set of electronic data records are electronic medical data records (EMR) of an individual patient.

According to a further embodiment of this aspect of the invention, the first set of data records relates to a virtual model of an apparatus and the second set of electronic data records are related to an individual apparatus.

The apparatus could be, for example, a car or a manufacturing machine. The second set of electronic data records could be, for example, service information, repair information or any other information about the individual car or manufacturing apparatus. The system could be advantageously used by a garage or factory for diagnosis or other purposes.

According to a further embodiment of this aspect of the invention, the system includes a data access unit for performing searches over the similarity network.

The searches may be performed by similarity-based or graph-based algorithms. As an example, the data access unit may receive a search query via the user interface and may then perform a random walk over the vertices of the similarity network in order to identify vertices that are similar to the search query.

According to a further embodiment of this aspect of the invention, the system includes a data entry unit, which is operable to perform upon data entry a search for concepts of the ontology that are similar to the data entry and for presenting to the user one or more concepts that are similar to the data entry.

The data entry unit can assist the user to annotate and classify his data entry with concepts. As an example, while a doctor types a report of a medical check, the data entry unit can return a list of concepts, which have been computed as being similar to the entered text. The user may then select one or more of the presented concepts, thereby annotating the entered text with the selected concepts.

According to a further embodiment of this aspect of the invention, the system includes a data summary unit for computing a summary of one or more second sets of electronic data records, wherein the summary includes a list of one or more graphical electronic data records being selected according to a predefined summary algorithm.

As an example, in the healthcare domain the data summary unit may be used to highlight anatomic parts of the virtual human body that have been computed as being relevant for the electronic medical data records of an individual patient or the electronic medical data records of a group of patients.

According to a further embodiment of this aspect of the invention, the annotation unit includes a first annotation unit for computing concept vectors of electronic medical data records and a second annotation unit for computing concept vectors of anatomic parts of a virtual human body.

According to a further embodiment of this aspect of the invention, the similarity network unit is operable to compute a static similarity network representing similarities of the second set of electronic data records, compute a dynamic similarity network representing similarities between preselected graphical data records of the first set of electronic data records and dynamically selected graphical data records of the first set of electronic data records, wherein the dynamically selected graphical data records are dynamically selected dependent on user interaction and link the dynamic similarity network to the static similarity network.

A static similarity network is understood as a network that does not change during user interaction. A dynamic similarity network is understood as a network that changes during user interaction. This allows for advanced user interfaces and improves the ease of use for the user. The graphical data records that are utilized for the similarity network can be adapted during user interaction.

As an example, in the healthcare domain the static similarity network would be computed from the electronic medical data records and the dynamic similarity network from the graphical data records of the virtual human body. The preselected graphical data records could be, for example, common or main anatomic parts of the virtual human body. The preselected graphical data records do not change while the user interacts with and navigates over the virtual human body. The dynamically selected graphical data records change during the user interaction with the virtual human body. The dynamically selected graphical data records may, for example, include only the anatomic parts that are currently visible to the user.

FIG. 1 shows a schematic illustration of a system 100 for analyzing electronic data records. The system 100 includes as annotation units a first annotation unit 110 and a second annotation unit 120. The first annotation unit 110 is operable to receive a first set 115 of electronic data records and the second annotation unit 120 is operable to receive a second set 125 of electronic data records. The first set 115 of electronic data records includes according to this embodiment of the invention graphical data records of a virtual model of a human body. The second set 125 of electronic data records includes according to this embodiment of the invention electronic medical records (EMR) such as text notes, lab test results and other unstructured electronic data records.

The first annotation unit 110 is operable to compute concept vectors 130 for the first set 115 of electronic data records. The coordinates of the concept vectors 130 represent scores of the concepts for the respective electronic data records of the first set 115. For each electronic data record of the first set 115, a concept vector 130 is computed. The concepts are part of an ontology 140 which might be, for example, the SNOMED-ontology.

The second annotation unit 120 is operable to compute concept vectors 135 for the second set 125 of electronic data records. The coordinates of the concept vectors 135 represent scores of the concepts in the respective electronic data records of the second set 125. For each electronic data record of the first set 115, a concept vector 130 is computed. The concepts are again part of the ontology 140.

In other words, the first annotation unit 110 and the second annotation unit 120 are operable to compute a structured representation of the first set 115 and the second set 125 of electronic data records based on the ontology 140. In other words, the concept vectors represent a 'bag of concepts' contained in the respective electronic data records. As an example, $(c_1, \ldots, c_n)$ may be the n concepts covered by the ontology 140. The concept vectors 130 and/or 135 of an electronic document d can be represented as a vector f in $R^n$ such that $f_i$ is a measure of whether or how frequent concept i is mentioned in the electronic document. Such measure can be, for example, a probability, that is, any number in [0, 1] but can also be related to the measure "term frequency-inverse document frequency" (TF-IDF) that is usually used in information retrieval.

The first annotation unit 110 and the second annotation unit 120 include one annotator for each concept of the ontology 140. In general, any function computing a coordinate $f_i$ of the concept vector f from an electronic document d is called an annotator. Such annotator is not limited to take the whole electronic document d as input but can also process chunks of an electronic document, such as part of an image or a sentence in a text.

The ontology 140 includes a list of tables defining concepts. The concepts are composed of unique IDs, a description n and a set of relationships, also denoted as attributes, with other concepts. These relationships can be of different types. Examples of such types are:

'is a' for an inheritance relationship meaning that a concept is a specialization of another concept. Bronchitis and disease are two concepts related by a 'is a' relationship: bronchitis 'is a' disease.

'part of' for an inclusion relationship meaning that a concept is part of another concept. The elbow concept for instance is a part of the arm concept.

The ontology 140 can be represented as a series of graphs, one for each relationship.

As a further illustration, it is assumed that a set of d words is given and a body of text documents $(d_1, \ldots, d_m)$ all represented as a bag of words vectors $d_i$, $i=1, \ldots, m$, where $d_{ij}$, $j=1, \ldots, d$ is the TF-IDF for term j in document $d_i$, a linear annotator is a linear function f from $R^d$ onto $\{-1,+1\}$ represented as a vector $(w,b) \in R^{d+1}$ such that $f(d_i)=\text{sign}(<w,d_i>+b)$, the output of f representing whether a given concept (for example, food) is mentioned in the document $d_i$ (returning +1) or not (returning −1). Such function f is widely used in text mining and is generally built using machine learning or pattern recognition techniques such as Support Vector Machines.

An annotator can therefore be regarded as a general tool to build a conceptual representation of a document. According to an embodiment of the invention, annotators on text documents can be built using pattern matching and a list of synonyms that are attached to each concept of the respective ontology 140. According to a further embodiment of the invention, annotators derived from machine learning algorithms can be used. Such annotators use a reference training set including manually annotated documents, that is, a list of pairs $(d_i, y_i)$ where $y_i \subset \{1, \ldots, n\}$ is the list of concepts in the ontology $(c_1, \ldots, c_n)$ that are referred by document $d_i$.

The system 100 includes a similarity network unit 150 being operable to compute a similarity network 160 representing similarities between the electronic data records of the first set 115 and the second set 125. The similarity network 160 is computed by means of the concept vectors 130 and the concept vectors 135 and by at least one relationship between the concepts of the ontology 140. The similarity network 160 includes vertices V that represent the electronic data records. Pairs of vertices V are connected by edges E that represent similarity values indicating a degree of similarity between the vertices V.

The system 100 further includes a similarity processing unit 170 being operable to receive the similarity network 160 as input and to perform similarity based algorithms over the similarity network 160. This allows for computing semantic similarities between the electronic data records of the first set 115 and the second set 125. The similarity processing unit 170 can interact with a data access unit 180, a data summary unit 185 and a data entry unit 190.

The similarity network 160 may be defined as a graph G=(V,E) where the vertices, also denoted as nodes, $V=(v_1, \ldots, v_m)$ are linked by edges $E \in V \times V$. Each edge $(v_i, v_j) \in E$ is associated with a similarity $s_{ij} \in R$ defining a similarity matrix $S=(s_{ij})_{i,j=1,\ldots,m} \in R^m \times R^m$, where $s_{ij}=0$ if $(v_i, v_j) \in E$. Since a similarity $s_{ij}$ is attached only to existing edges E, it does not fulfill any transitivity condition. For example, if $s_{ij}$ and $s_{jk}$ are both large, it does not necessarily mean that $s_{ik}$ is large. $s_{ik}$ is indeed zero if there is no edge between $v_i$ and $v_k$. For the calculations of "intuitive" similarities, the similarity processing unit 170 may use propagation techniques as will be explained later in more detail.

In the context of medical and anatomic electronic data records, the vertices of G correspond to medical entries or anatomic parts. More generally, any electronic data record mapped onto a concept vector is considered as a vertex of the similarity network. The ontology 140 can be interpreted as a series of graphs $G_S^a=(V,E^a)$ over a set of concepts $V=(c_1, \ldots, c_n)$, where the index a runs over the list of attributes. The attributes express characteristics of a concept in the form of relationships. The set $E^a$ is defined as: $(v_i,v_j) \in E^a$ if $v_i$ and $v_j$ are "linked" by attribute/relationship a. Examples of attributes include 'is a' for the inheritance relationship or 'caused by' for the cause-effect relationship. In the following, the elements of the incidence matrix are denoted by $w_{ij}^a \in \{0, 1\}$, which are related to the relationship a: $w_{ij}^a=1$ iff $(c_i,c_j) \in E^a$. A similarity network $G_S$ on SNOMED may be computed as the union of all graphs $G_S^a$'s: $G_S=(V, \cup_a E^a)$. The weight along the edge $(c_i,c_j)$ is then computed as:

$$w_{ij} = \sum_a \lambda_a w_{ij}^a, \quad w_{ii} = 0 \qquad (1)$$

where $\lambda_a$ are non-negative coefficients to be determined. If all attributes have the same importance, preferably a constant value $\lambda_a=1$ for all a's is considered. Otherwise, the more important attributes should be given more weight by having larger $\lambda_a$'s. This similarity network $G_S$ can be used, for example, to perform searches over SNOMED-terms by means of the data entry unit 190 as will be described later in more detail. The similarity network $G_S$ also defines the basic structure, from which a similarity on the concept vectors 130 and 135 can be computed by the similarity processing unit 170.

According to an embodiment of the invention the Laplacian matrix $L \in R^m \times R^m$ is used, which is defined as:

$$L_{ij} = \begin{cases} w_{ij} & \text{if } i \neq j \\ -\sum_{k=1, k \neq i}^{m} w_{ik} & \text{if } i = j \end{cases} \qquad (2)$$

It has many interesting properties related to the structure of the graph. Its exponentiation $M=\exp^{\beta L}$ leads to a positive definite matrix: $\forall f \in R^m$ $$\sum_{i,j=1}^{m} f_i f_j M_{ij} \geq 0$$

that can be used to define a kernel, that is a dot product, between two concept vectors $f_i$ and $f_j$ as:

$$k_M(f_i, f_j) = \sum_{l,p=1}^{m} f_{il} f_{jp} M_{lp} \qquad (3)$$

If W, the similarity matrix derived from the $w_{ij}$'s, is symmetric, then $-L$ can be directly used as a measure of similarity. The above equation (3) defines a similarity value $k_M$ between electronic data records by taking into account the structure imposed by SNOMED. The non-diagonal terms in the matrix M establish links between concepts that are different but that are linked either directly or indirectly in the graph. The user can change the influence of the different attributes based on the nature of the information. As an example, if a user is interested in the causal links, it might be sufficient to focus on the corresponding part of the similarity network 160, that is, the similarity graph defined by the attribute 'caused by', that is, setting $\lambda_a=0$ in (1) for all a's except when a refers to the 'caused by' relationship, in which case $\lambda_a=1$.

Automatic determination of the $\lambda_a$'s can be done if a referenced similarity $k_O(f_i,f_j)$ is available. In that case, techniques such as target alignment as described by Nello Cristianini, Andre Elisseeff, John Shawe-Taylor, and Jaz Kandola, in *On kernel target alignment*, Proceedings Neural Information Processing Systems (NIPS), 2001 could be used to derive the value of the $\lambda_a$'s that maximize the correlation between $k_M$ and $k_O$. When indirect measures are available, such as described by Patrick Ruch, Julien Gobeill, Imad Tbahriti, Robert Baud, and Antoine Geissbühler in *Automatic assignment of snomed categories: Preliminary and qualitative evaluations*, Semantic Mining Conference on SNOMED CT, October 2006, the $\lambda_a$'s can be tuned to increase the performance of the information system 100. As a default setting, the system 100 may assumes that all $\lambda_a$'s are set to 1.

Figure 2:
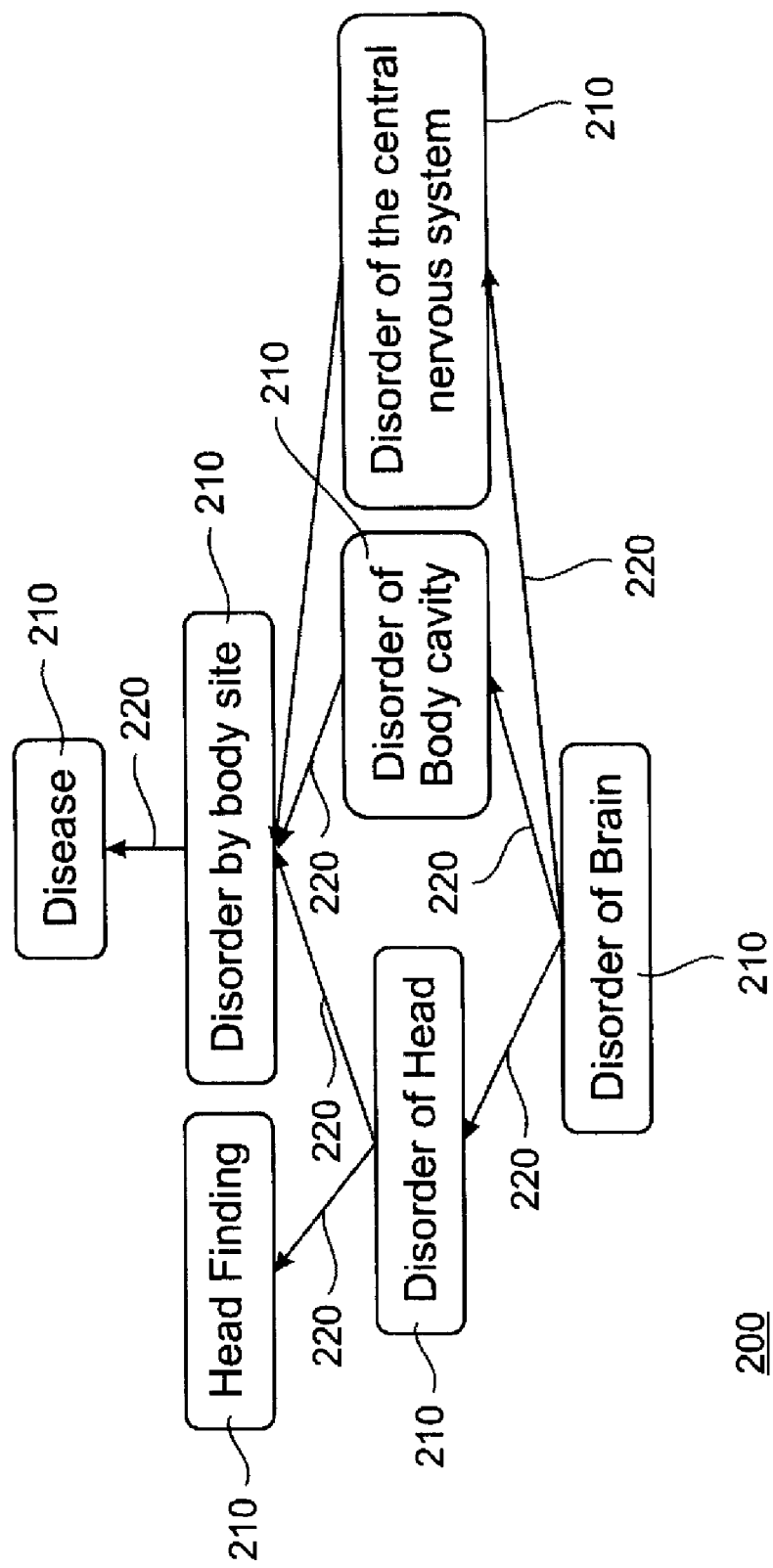
FIG. 2 shows a graph of the root concept disease including "Is a" relationships.

FIG. 2 shows a graph 200 as an example for an "Is a" relationship. The graph 200 includes concepts 210 such as disease and disorder by bode site. The concepts 210 are linked by the "Is a" relationship 220 indicated by arrows.

Figure 3:
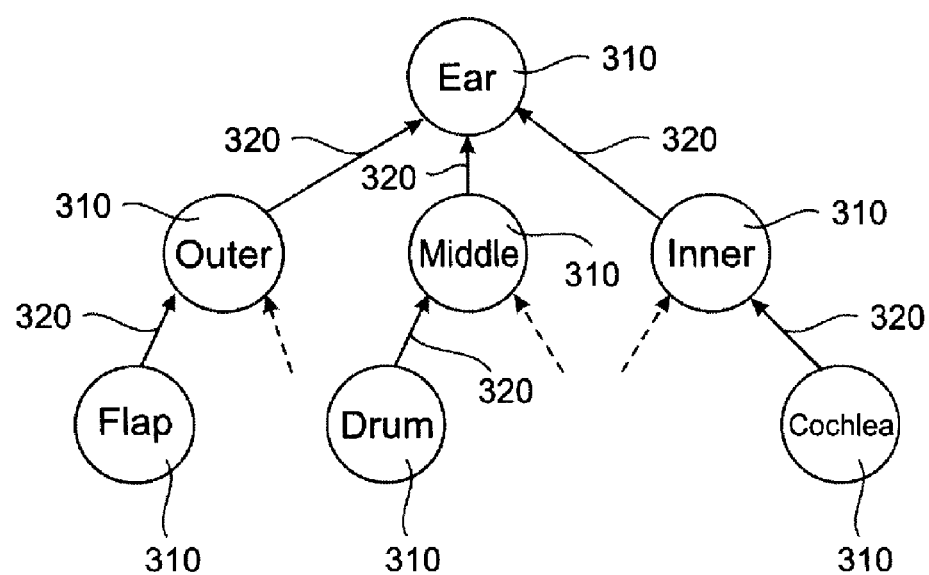
FIG. 3 shows a graph of the root concept ear including "Part of" relationships.

FIG. 3 shows a graph 300 as an example for a "Part of" relationship. The graph 300 includes concepts 310 such as ear, outer ear and inner ear. The concepts 310 are linked by the "Part of" relationship 320 indicated by arrows.

Figure 4:
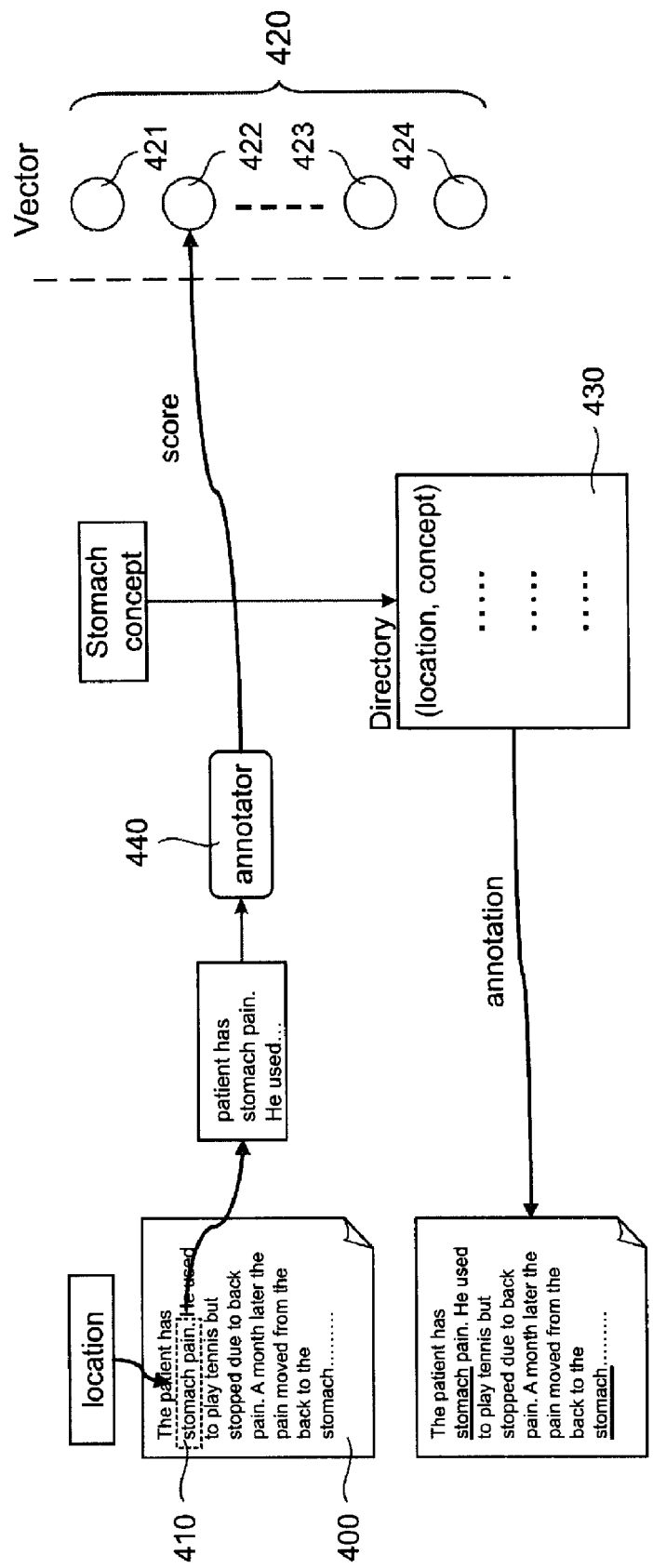
FIG. 4 illustrates an operation mode of an annotation unit.

FIG. 4 illustrates an operation mode of the second annotation unit 120 of FIG. 1 in more detail. In this example the second annotation unit 120 takes an electronic medical record 400 including text as input. In general, the second annotation unit 120 can work with the whole electronic medical record 400 or first extract a window 410 around the location of interest. Then, the second annotation unit 120 computes a score 422 measuring if or how likely a concept (here stomach) is mentioned in the electronic medical record 400. Further scores, for example, scores 421, 423 and 424, from all the concepts of the respective ontology are combined to compute the concept vector 420 for the electronic medical record.

In addition, the second annotation unit 120 runs a directory 430. The directory 430 stores a location-concept pair for each occurrence of the respective concept in the electronic medical record 410. In this example the location could be stored in the form of page and line numbers of the respective occurrence of the respective concept. The directory 430 may have the form of a table. The directory 430 can later be used to annotate the electronic medical record 410 with respect to a selected concept. As an example, the directory 430 can be used to return all locations that have been detected as related to the selected concept. Here, location is meant in a broad sense: it can be the logical address of the electronic medical record with the number of characters from the beginning of the electronic medical record until the concept appears. Many location-concept pairs can refer to the same electronic medical record and the same concept but with different locations.

The annotator 440 may be described as a function that returns a real number from the electronic medical record 410 or from a part of the electronic medical record 410 and a location. The latter is optional but when it is given, a mechanism to extract local information from the electronic medical record needs to be defined. In the case of text documents, the extraction can be performed using boundaries (for example, two sentences before and after the location in the text). For an XML file, the extraction can be restricted to the scope (that is, the type) of the document as tagged in the file.

Figure 5:
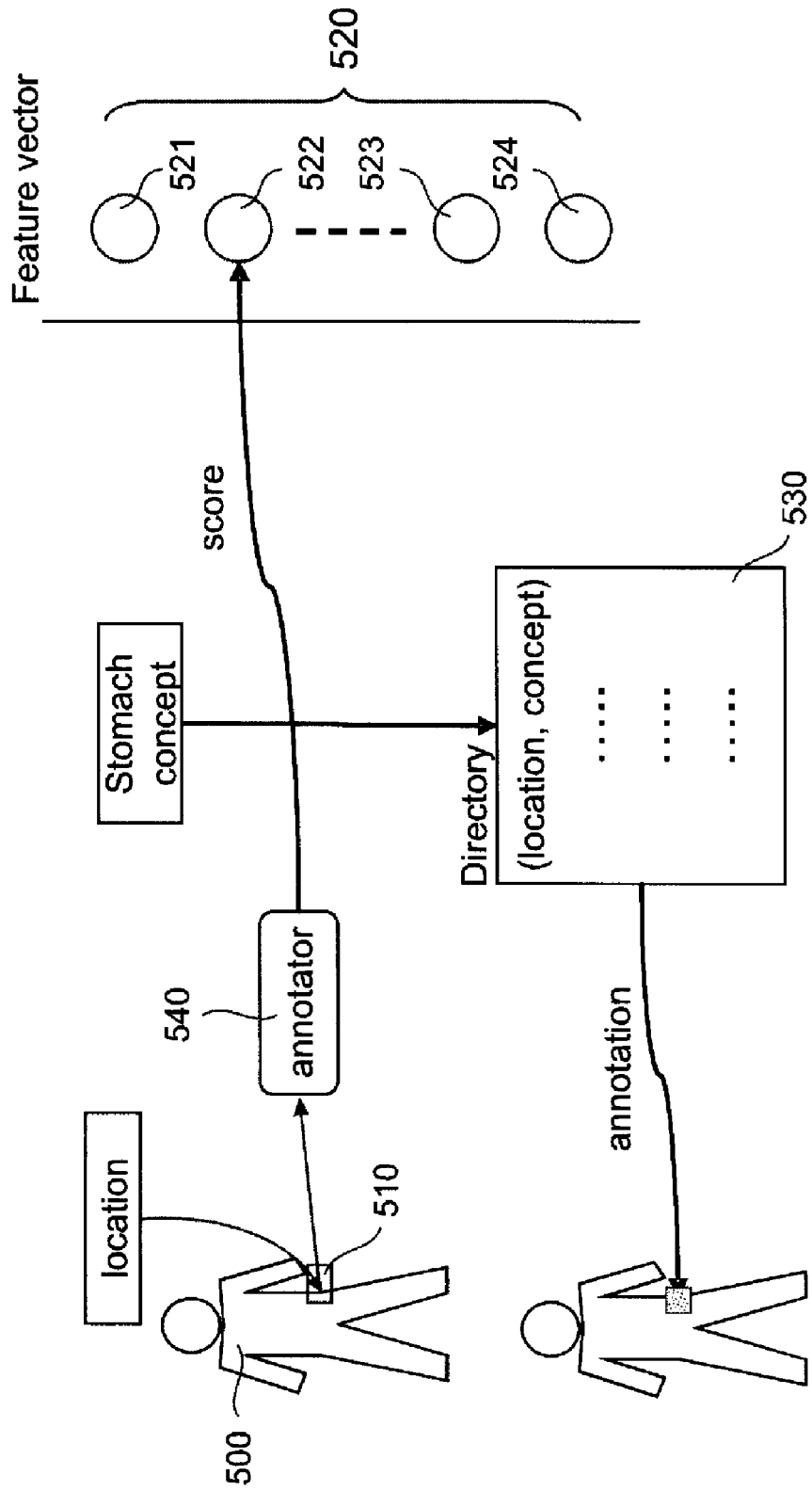
FIG. 5 illustrates an operation mode of another annotation unit.

FIG. 5 illustrates an operation mode of the first annotation unit 110 of FIG. 1 in more detail. In this example the first annotation unit 110 is provided for annotating graphical electronic data records 510 of a virtual human body 500. The first annotation unit 110 takes the graphical electronic data record 510 of a graphical data record repository. The graphical data records 510 relate to organs or anatomic parts of the virtual human body. The first annotation unit 110 computes a concept vector 520 for the graphical electronic data records 510, that is, for the anatomic parts of the virtual human body. Furthermore, the graphical electronic data records 510 include location data corresponding to the position of the respective anatomic parts or organs. The location data can be used to map any click on the virtual human body 500 onto a name of the corresponding organ or anatomic part. The location data correspond to a 2-dimensional or 3-dimensional model of a human body and may for example, include 3-dimensional coordinates locating a point or an object of an OpenGL model.

The first annotation unit 110 computes a score 522 measuring if or how likely the respective anatomic part of the virtual human body relates to the concept of the respective annotator, that is, in this example to the concept "stomach." The scores from all the concepts of the ontology 140, for example the further scores 521, 523 and 524, are combined to compute the concept vector 520 for the graphical electronic data record 510.

A directory 530 stores one or more location-concept pairs for each part of the virtual human body 500. In this example the location could be stored in the form of 2-dimensional or 3-dimensional coordinates of the respective part of the virtual human body 500. The directory 530 may have the form of a table. The directory 530 can later be used to annotate the graphical electronic data record 510, that is, the selected part of the virtual human body, with concepts that are considered similar to the selected part. As an example, the directory 530 can be used to return all locations, that is, all parts of the virtual human body 500 that have been detected as related to the selected concept "stomach."

The principle of the first annotation unit 110 and the second annotation unit 120 is similar. Given an electronic data record and a corresponding location, the first annotation unit 110 and the second annotation unit 120 will compute a score for this location to be related to the respective concept (here stomach). Even though the location does not correspond to the physical location of a stomach, the score might still be high. Parts of the stomach for instance are expected to be related to the concept of stomach.

Figure 6:
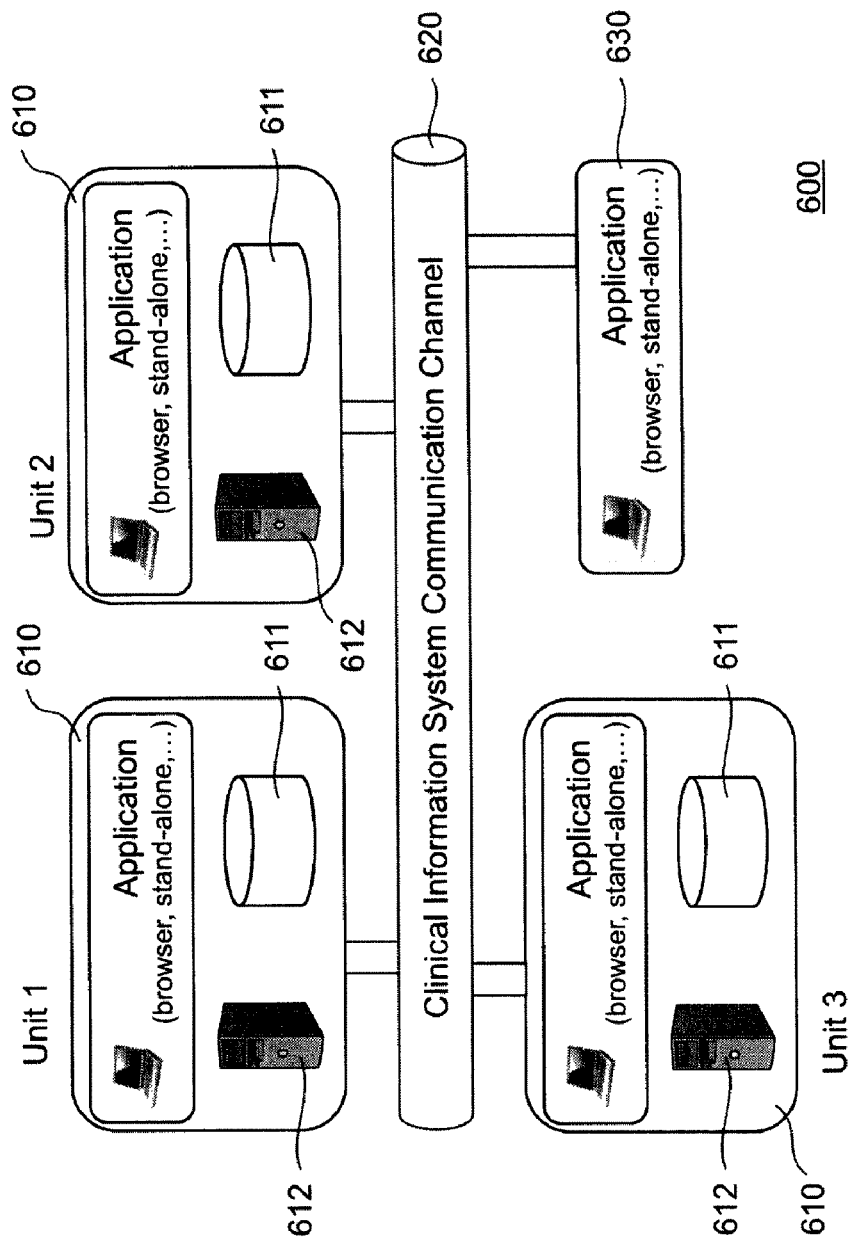
FIG. 6 illustrates the structure of a clinical information system.

FIG. 6 illustrates the structure of a clinical information system 600. It includes units 610 that may represent a hospital department such as the urology department. More generally the units 610 may refer to any care delivery organization with a local information system. All units 610 have a local storage system 611 containing electronic medical data records of patients and processing units 612. As an example, one of the units 610 could be a lab unit in a hospital that manages the databases storing the results of the lab tests. The units 610 may communicate with each other by means of a communication channel 620. The communication channel 620 can take the form of a peer-to-peer communication or can represent a centralized database regularly polling all data from the units 610 and storing all existing electronic medical records. The patients can be identified by means of a unique ID shared by all units 610. A user of the clinical information system 600 can access the electronic medical records about a patient from a unit 630, for example, by means of a laptop using an electronic medical record application.

Figure 7:
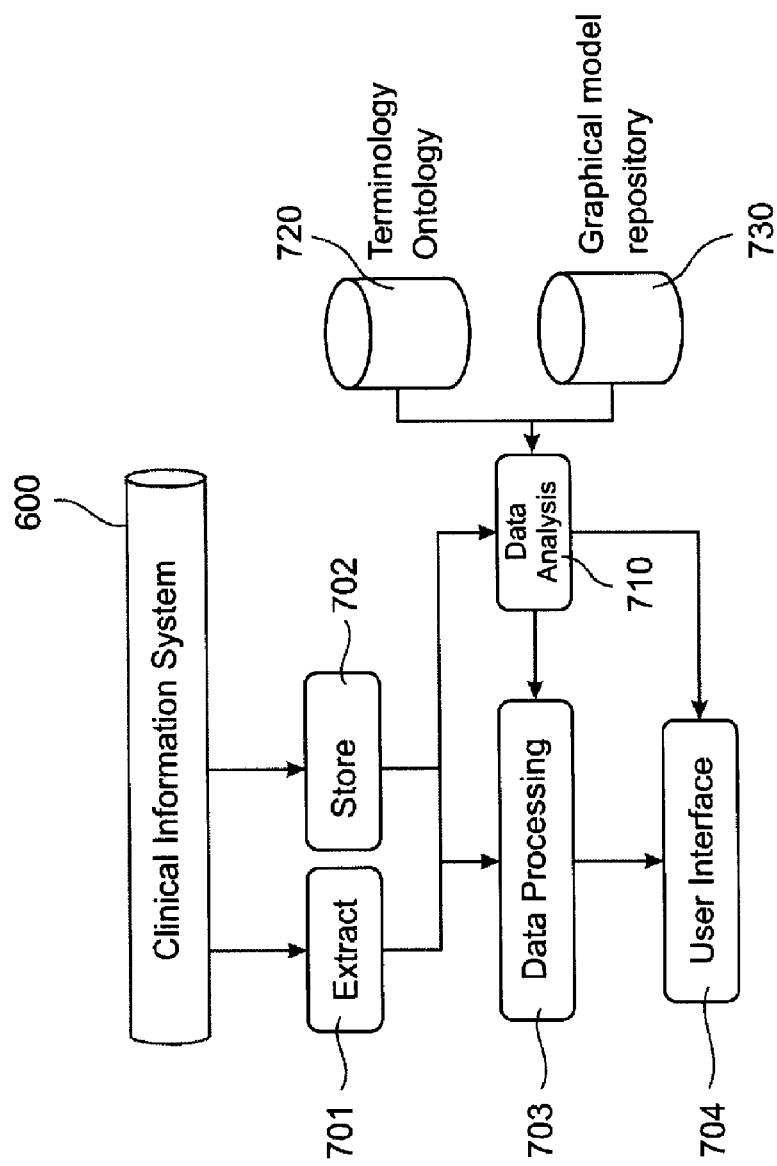
FIG. 7 shows an electronic medical record application.

Such an electronic medical record application 700 is illustrated in FIG. 7. It includes an extraction component 701 that loads data from a physical (hardware) or virtual source (software), a store component 702 that writes or sends data to a physical or virtual source, a data processing component 703 that transforms the data to be shown to the user and a user interface 704 that enables user interaction with the data either to access it or to change it.

The electronic medical record application 700 includes a data analysis component 710 connecting to the data processing component 703 and the user interface 704. The data analysis component 710 extracts data from the same sources as the application it links to. Such data includes XML files following formats such as the Standardized Use of Patient model or the Clinical Document Architecture model of Health Level 7. The data analysis component 710 is further connected to an ontology database 720 storing data of an ontology such as SNOMED and a graphical object database 730 storing graphical electronic data records of a virtual human body. The data analysis component 710 may be a system 100 for analyzing electronic data records as described with reference to FIG. 1.

Figure 8:
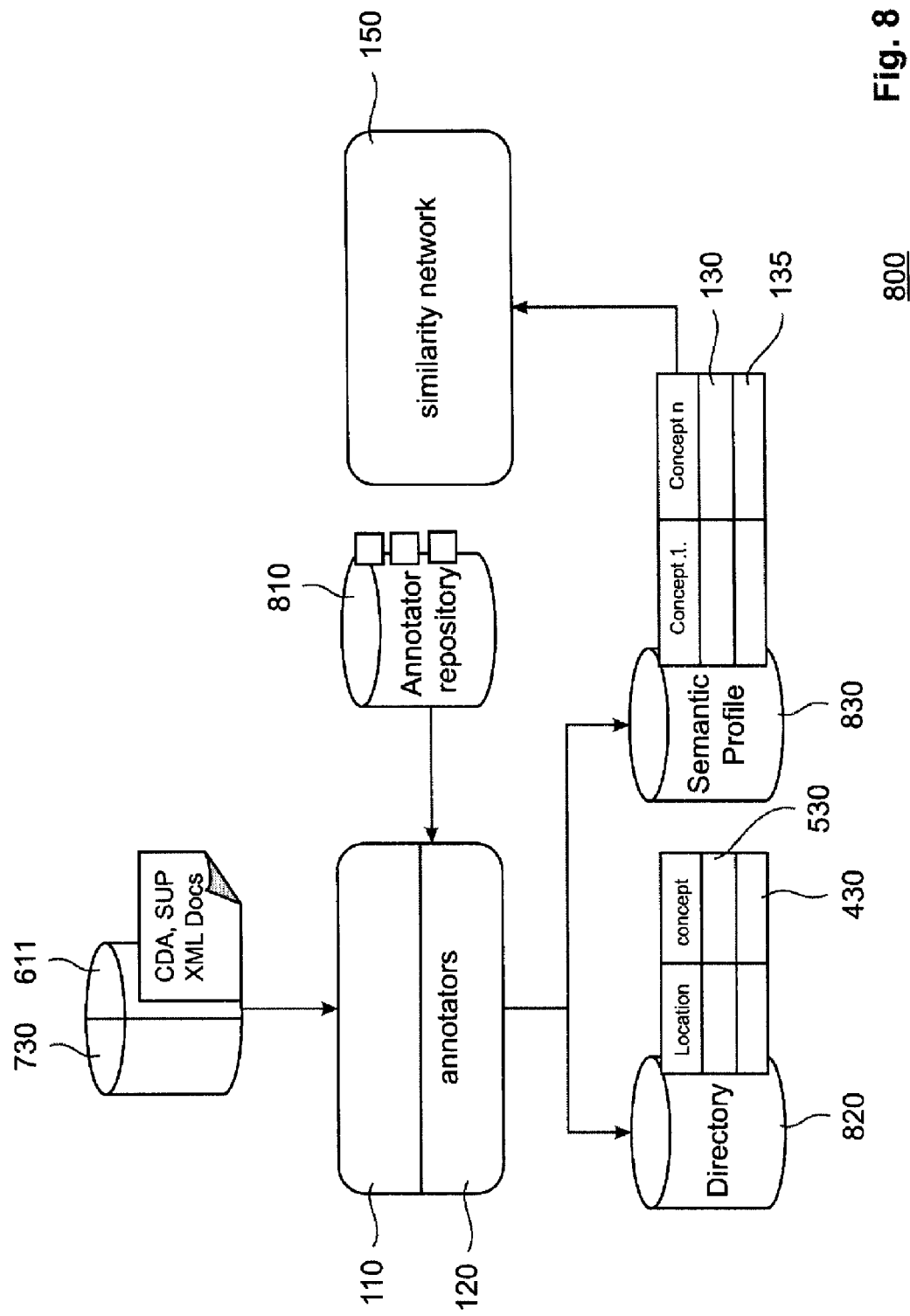
FIG. 8 shows a storage arrangement for the system of FIG. 1.

FIG. 8 illustrates an exemplary embodiment of a storage arrangement for the system 100 of FIG. 1. The storage arrangement 800 includes an annotator repository 810 for storing all annotators that have been computed by the first annotation unit 110 and the second annotation unit 120 to detect concepts, for example, SNOMED concepts, from EMR received for example, from the local storage systems 611 or from graphical electronic data records received for example, from the graphical object database 730.

A directory database 820 including directories 430 and 530 is built as described with reference to FIG. 4 and FIG. 5.

The concept vectors 130 computed by the first annotation unit 110 and the concept vectors 135 computed by the second annotation unit 120 are stored in a semantic profile database 830. When new annotators are created, the semantic profiles stored in the semantic profile database 830 can be replaced by updating the coordinates computed by the new annotators. When a new electronic data record, for example, a new EMR, comes in, all annotators of the annotator repository 810 are used to build the corresponding concept vector 130 or 135. The concept vectors 130 and 135 are fed into the similarity network unit 150 that computes similarities between the graphical electronic data records 115 and the EMR 125.

Figure 9:
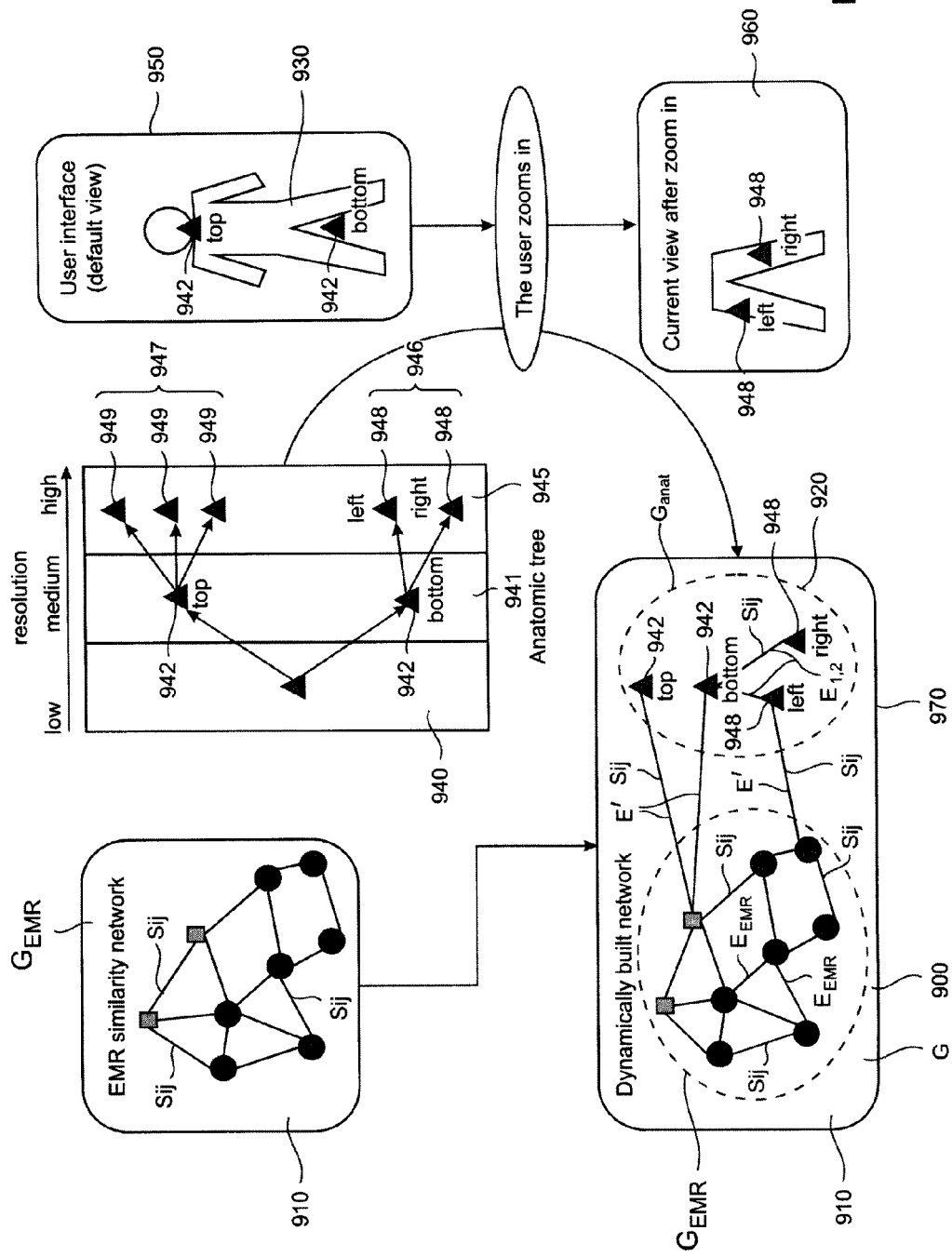
FIG. 9 illustrates a similarity network composed of a static similarity network and a dynamic similarity network.

FIG. 9 illustrates a similarity network G, also denoted with reference numeral 900, according to an embodiment of the invention. The similarity network G can be decomposed into two components: one sub-network $G_{EMR}$ denoted as static similarity network, also denoted with reference numeral 910, whose structure does not change while the user interacts with the system 100; and another sub-network Ganat, denoted as dynamic similarity network, also denoted with reference numeral 920, whose structure changes while the user navigates over a virtual human body 930 and which is computed based on the user interaction with the virtual human body 930.

The static similarity network $G_{EMR}=(V_{EMR},E_{EMR})\subset G$ contains the concept vectors 135 computed from the second set 125 of electronic data records, that is, from the electronic medical data records. The static network $G_{EMR}$ does not contain the concept vectors 130 computed from the first set 115 of electronic data records, that is, from the graphical electronic data records of the virtual human body 930. Each vertex, also denoted as node, of the static similarity network $G_{EMR}$ represents therefore an EMR or a part of an EMR with its corresponding location within the EMR along with the EMR-address. A similarity value $s_{ij}$ between two EMR $d_i$ and $d_j$ and their respective concept vectors $f_i \in R^d$ and $f_j \in R^n$ can be computed as:

$$s_{ij} = k(f_i, f_j) \quad (4)$$

where k is a kernel. Such kernel k may be, for example, the Euclidean dot product:

$$k(f_i, f_j) = \langle f_i, f_j \rangle = \sum_{l=1}^{d} f_{il} f_{jl}.$$

According to a preferred embodiment of the invention, kernels $k_M$ as defined in equation (3) and its variants are used to compute similarity values $s_{ij}$. Such kernels $k_M$ measure the semantic similarity of the two concept vectors $f_i$ and $f_j$. Other similarity measures such as correlation can also be used to compute similarity values $s_{ij}$, for example:

$$s_{ij} = \frac{k(f_i, f_j)}{\sqrt{k(f_i, f_i) k(f_j, f_j)}}.$$

The scope of the static network $G_{EMR}$ can be changed based on the user requirements. As an example, filtering can be applied first on the EMR to retain only EMR generated within a time period or EMR coming from one particular organization. In general, all kinds of rules and restrictions can be used to limit the scope of the similarity network G to the domain of interest.

The static network $G_{EMR}$ and more generally the network G itself are different from the SNOMED network $G_S$. While the SNOMED network $G_S$ is computed from or built on single SNOMED concepts, the static network $G_{EMR}$ and the network G are constructed from electronic data records such as EMR and graphical data records. A SNOMED concept $c_i$ can be considered as a feature vector $f_i$ by setting $f_{ij}=0$ if $i \neq j$, and $f_{ii} = \max_{f_i \in G} f_{ii}$, wherein the maximum is taken over all concept vectors encoded into G. This induces a sub-graph $G_{\tilde{S}}$ of G over SNOMED concepts whose similarities are different from the ones in $G_S$.

The system 100 computes the static network $G_{EMR}$ regularly once the EMR 125 are updated with a new entry. The $G_{EMR}$ preferably does not change during the consultation or the navigation.

The dynamic similarity network $G_{anat}$ represents an anatomic tree of the virtual human body 930 and is an acyclic graph $G_{anat} = (V_a, E_a)$ where $V = (a_1, \ldots, a_d)$ are the anatomic parts $a_i$'s such as nose or ear, and $(a_i, a_j) \in E$ if $a_j$ is a part of $a_i$. The root vertex (root node) $a_1$ is a generic concept such as "anatomic part." According to a preferred embodiment of the invention V is divided into two subsets $V_1$ and $V_2$. The subset $V_1$ is a predefined set of anatomic parts. The predefined set may include the common anatomic parts as defined by a medical expert. The subset $V_1$ is preferably fixed during the user interaction and may generally represent the set of anatomic parts that is visible when the virtual human body 930 is first presented to the user, that is, when the system 100 is started.

The subset $V_2$ corresponds to the anatomic parts that are currently shown to the user. The subset $V_2$ changes over time while the user interacts with the system 100. As an example, zooming on the skeleton of the hand would reveal a series of bones that were not shown when the system 100 started. The series of bones would be included into the subset $V_2$. On the other hand anatomic parts that disappear during the user interaction are removed from the subset $V_2$. In the following $E_1$ and $E_2$ respectively denote the set of edges derived from Ganat restricted on the subset $V_1$ and the subset $V_2$ respectively. The structure of the dynamic similarity network $G_{anat}$ can be derived from existing ontologies. The Foundational Model for Anatomy for instance can be used to provide the 'part of' relationship for all anatomic parts. Each node of the dynamic similarity network $G_{anat}$ is preferably augmented with a location information that indicates where the corresponding part is shown on the virtual human body. This enables the annotators to easily find what anatomic part the user is interested in while clicking on the body part.

Referring back to FIG. 9, a window 940 illustrates how the number of vertices of the dynamic similarity network $G_{anat}$ is adapted during user interaction. The medium part 941 of the window 940 represents the subset $V_1$ of anatomic parts that are visible when the virtual human body 930 is first presented to the user, that is, when the system 100 is started. This could be a default setting and involves a medium resolution on the corresponding display. In this default setting, only the vertices 942 of the subset $V_1$, denoted with top and bottom, are allocated to the dynamic similarity network $G_{anat}$. When the user zooms in, the number of vertices of the dynamic similarity network $G_{anat}$ is enlarged by a subset $V_2$ of anatomic parts. The right part 945 of the window 940 illustrates two examples for the subset $V_2$.

A first subset $V_2$ denoted with 946 includes two vertices 948, also denoted with "left" and "right." The first subset 946 is added to the dynamic similarity network $G_{anat}$ when the user zooms on the bottom part of the virtual human body 930.

A second subset $V_2$, denoted with 947, includes three vertices 949. The second subset 946 is added to the dynamic similarity network $G_{anat}$ when the user zooms on the top part of the virtual human body 930.

The window 950 of FIG. 9 illustrates a default view on the virtual human body 930 with the corresponding vertices 942. When the user zooms in on the bottom part of the virtual human body 930, a zoomed view with higher resolution is presented to the user, which is illustrated in window 960. The zoomed view includes the additional vertices 948. The window 970 illustrates the corresponding similarity network G including the static network $G_{EMR}$ and the dynamic network $G_{anat}$. The dynamic network $G_{anat}$ includes the vertices 942 of the first subset V1 and the vertices 948 of the second subset V2.

Hence, the similarity network G is, according to the above described embodiment of the invention, an interactive similarity network. In other words, it is at least partly computed and changed during the user interaction. The similarity network G can be defined as a graph $G_i = (V_i, E_i)$, where $V_i = V_1 \cup V_2 \cup V_{EMR}$ and $E_i$ are defined as the union of $E_{EMR}$, $E_1$, $E_2$, $E_{12}$ and E'. E' is defined as follows: an edge is in E' if it links a vertex of $V_1 \cup V_2$ to a vertex in $V_{EMR}$. In other words, an edge belongs to E' if it links a vertex of the dynamic similarity network $G_{anat}$ whose vertices represent parts of the virtual human body to a vertex in the static similarity network $G_{EMR}$ whose vertices represent EMR. $E_{12}$ is defined as follows: an edge is in $E_{12}$ if it links a node of $V_1$ to a node in $V_2$.

Referring back to FIG. 9, there are three edges E' that link the static similarity network $G_{EMR}$ to the dynamic similarity network $G_{anat}$.

As mentioned, the annotators of the first annotation unit 110 map graphical anatomic parts of the virtual human body onto concepts of an ontology, for example, on the concepts of the SNOMED ontology. In other words, the annotators of the first annotation unit 110 compute a concept vector for each node in $V_1 \cup V_2$. These concept vectors can be used to compute or estimate a similarity with the nodes of the static network $G_{EMR}$.

The similarity network G is the result of the merge of two similarity networks, that is, from the static network $G_{EMR}$ computed from the EMR and from the dynamic similarity network $G_{anat}$. The dynamic similarity network $G_{anat}$ represents a sub tree extracted from the anatomic tree by considering only the predefined nodes and the nodes that are currently shown or visible to the user. Each of the nodes of the dynamic similarity network $G_{anat}$ corresponds to a region or location of the virtual human body and is transformed into a concept vector 130 using the first annotation unit 110. These concept vectors 130 are then added to the static similarity network $G_{EMR}$ to create the similarity network G.

The similarity network G can be used for different purposes. In the following sections, three exemplary embodiments of such use are described, which may be performed by the data access unit 180, the data summary unit 185 and the data entry unit 190 of FIG. 1.

The data access unit 180 may perform information retrieval in a broad sense and uses the similarity network 160 to process queries.

The similarity processing unit 170 may use similarity based algorithms, in particular graph-based search algorithms, for computing semantic similarities between the vertices of the similarity network G. One preferred technique is manifold ranking as described, for example, in Dengyong Zhou, Jason Weston, Arthur Gretton, Olivier Bousquet, and Bernhard Schölkopf, *Ranking on data manifolds*, Tech. Report 113, Max Planck Institute for Biological Cybernetics, Tübingen, Germany, June 2003.

Graph-based search algorithms perform a random walk over the vertices of the similarity network G, wherein the transition probabilities between the respective vertices are computed from the similarities between the respective vertices.

Let $v_1, \ldots, v_m$ be the set of vertices in the similarity network G and $s_{ij}$ a set of similarities between $v_i$ and $v_j$. Vertices that are activated can be represented by means of a vector $p \in R^m$, wherein $p_i = 0$ when $v_i$ is not activated and $p_i = 1$ when $v_i$ is activated. The activation of vertices may be performed by user interaction, for example, by clicking on a part of the virtual human body in order to initiate a search for vertices that are similar to the activated vertex. The coordinate $p_i$ can be interpreted as the probability for $v_i$ to be activated. A random walk through the similarity network G is a propagation mechanism where each vertex has a probability to activate its neighbor vertices based on its similarity with the neighbor vertices. The propagation mechanism can be formulated in the following way:

If p(t) denotes the probability of a vertex being activated at iteration t, then the probability p(t+1) that the same vertex is activated in the next iteration t+1 is $$p(t+1) = \alpha A p(t) + (1-\alpha)p \quad (5)$$

and p(0)=p. The matrix A can be interpreted as the transition matrix:

$A_{ij} = P(\text{activate}(v_i) | \text{activate}(v_j))$, wherein activate(v) refers to whether the vertex v is activated or not. The factor $\alpha$ controls the trade-off between the constant activation p and the propagation mechanism. There are different techniques to compute the matrix coefficients $A_{ij}$. One method includes computing a non normalized transition matrix A from the similarities $w_{ij}$ as $\tilde{A}_{ij} = \exp(-\gamma w_{ij})$ where $\gamma$ is a scaling factor. A is then calculated as $$A_{ij} = \tilde{A}_{ij} \Big/ \sum_j \tilde{A}_{ij}.$$

Figure 10:
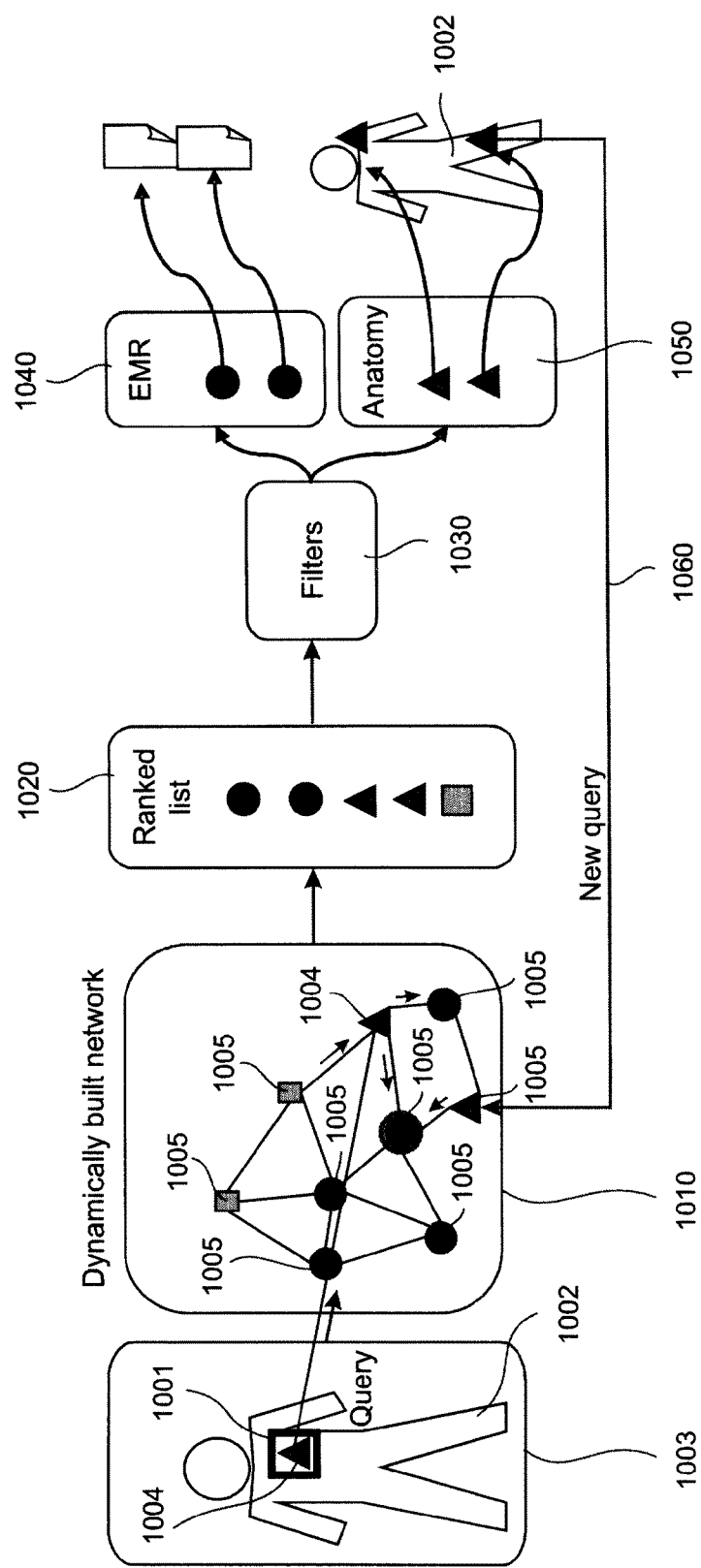
FIG. 10 illustrates an operation mode of a data access unit of a system of FIG. 1 for performing searches over a similarity network.

An example for the above approach is illustrated in FIG. 10. It can be implemented as a mode of operation in the data access unit 180 of FIG. 1.

The user enters a query 1001 by means of a user interface, for example, by means of the user interface 704, to the data access unit 180. This query can be, for example, performed by clicking on a virtual human body 1002 displayed on a display 1003. The query 1001 activates a vertex 1004 of the dynamic similarity network $G_{anat}$. The query 1001 is processed by the data access unit 180, which involves the similarity processing unit 170 and the similarity network unit 160. The similarity network unit 160 has computed a similarity network 1010. The similarity processing unit 170 takes the vertex 1004 as input and computes similarities of the vertex 1004 with the other vertices of the similarity network 1010. The similarities of the vertex 1004 with the other vertices 1005 of the similarity network 1010 may be computed by a graph-based search algorithm as described above. The graph-based search algorithm performs a random walk over the vertices 1005 of the similarity network 1010. As a result of the search, the similarity processing unit 170 returns search results 1020 as a ranked list of vertices being considered most similar to the vertex 1004.

The vertices 1004 and 1005 of the similarity network 1010 may represent different kinds of electronic data records. This is illustrated in FIG. 10 by different symbols for the vertices 1004 and 1005. Vertices 1005, being illustrated by a triangle, represent anatomic parts of the virtual human body 1002. Vertices 1005, being illustrated by a circle, represent electronic medical data records. Vertices 1005, being illustrated by a square, represent lab test results. The vertex 1004, being illustrated by a triangle, represents the anatomic part of the search query.

The data accessing unit 180 may include one or more filters 1030 that filter and/or categorize the search results. In this example, the filters 1030 separate EMR 1040 from anatomic parts 1050. The EMR 1040 may be displayed as text documents and the anatomic parts 1050 may be highlighted on the virtual human body 1002.

Once the search results 1020 have been presented to the user, the user can further refine the search, for example, by changing the view on the virtual human body 1002 and by selecting the anatomic parts or documents that seemed the most relevant for the initial query. This corresponds to adding more activation vertices to the similarity network 1010, that is, more coordinates of p are set to 1. In FIG. 10 that step is illustrated by an arrow 1060 being directed from the virtual human body 1002 to the similarity network 1010. Such search technique can also be used on the SNOMED similarity network $G_S$ directly. By considering $G_{\bar{S}}$, the embedding of $G_S$ into $G_{EMR}$, and its similarity with $G_{anat}$, a link between the visual representation of the human body and the SNOMED terminology can be established. A search can be performed directly from the virtual human body 1002 or via free text. Such techniques can also be used for data entry and automatic annotation and will be explained below in more detail. Furthermore, a SNOMED term search can be performed directly on the similarity network G, that is, the full similarity network containing all the documents of interest as well as $G_{\bar{S}}$ and $G_{anat}$. In that case, the result of the search would contain not only terms that are semantically similar to the query but also terms that are relevant based on the medical history under consideration.

The above described information retrieval technique can be used with the similarity network G. A user can activate one vertex of the similarity network G, which may be a vertex corresponding to an anatomic part of the virtual human body by clicking on the virtual human body. According to another embodiment, the user may activate a vertex of the similarity network G by typing some text. The text can be mapped by the second annotation unit 120 into a concept vector and could be added as a new activated node of the similarity network G. After one or more vertices of the similarity network G have been activated, the similarity processing unit 170 may perform a similarity search with respect to the activated vertices. As a result, the data access unit 180 will return a ranked list of vertices. Some of the vertices may correspond to EMR, for example, free texts or lab test results. Other vertices will correspond to anatomic parts of the virtual human body. The user can specify the information he desires from the search so that the list of resulting vertices can be filtered and can show only the desired type of information. Such search specification may, for example, specify that the user is only interested in anatomic parts of the virtual human body or in lab results of the last three months. In addition, the user may limit the scope of the search by specifying one or more attributes/relationships of the similarity network G. As an example, if the user is mainly interested in the causes of the disease, the similarity network G would will be recomputed or updated according to equation (1). This leads to a new propagation equation (5) specifically for the 'caused by' attribute/relationship. The result of the search would then be only related to the causes, for example, root causes, indirect or direct causes or consequences.

Figure 11:
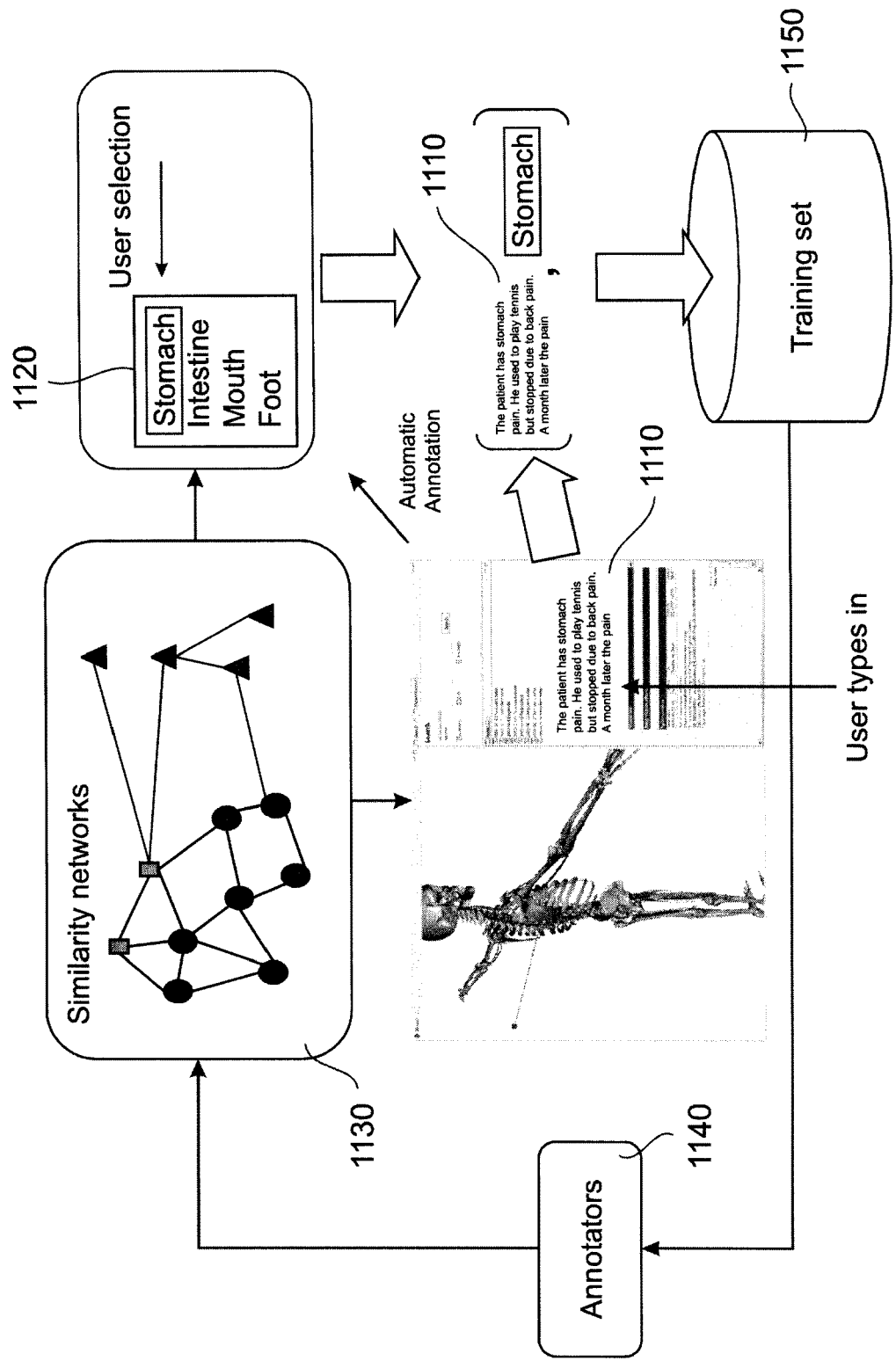
FIG. 11 illustrates an operation mode of a data entry unit of a system of FIG. 1.

FIG. 11 illustrates a mode of operation of the data entry unit 190. While the user types some text 1110, for example, while a doctor types a report of a medical check, the system 100 can run in the background the first annotation unit 110 and the second annotation unit 120. Preferably, the first annotation unit 110 and the second annotation unit 120 run only annotators 1140, which are deemed the most appropriate in the context of interest. These annotators 1140 will be processed by the similarity network unit 150, resulting in a similarity network 1130. The system 100 returns a list 1120 of concepts, which have been computed as being most similar to the text 1110. This list 1120 of concepts is computed by performing a search over SNOMED-concepts using a similarity based algorithm as described above. By providing a search on the fly, the user can directly annotate while writing. The user can select the concept of the list 1120, which he considers most important to the text 1110 that he just typed in. In this example, the user has selected the concept stomach as most relevant. Accordingly, a document-concept pair, in this example the text 1110 and the concept stomach is added to a training set 1150, which can be used to train the annotators 1140. The training set 1150 can later be used to retrain the existing annotators 1140. This gives the user the possibility to change, adapt and train the system 100 and to improve the detection of concepts that are frequently used. By aggregating the results from many users, the training sets 1150 get larger and the annotators 1140 get more accurate.

The concepts that are picked by the user can also be highlighted on the human body when appropriate. When building the annotators 1140, the system 100 creates and maintains a table containing the pairs (location, concept) that have been detected. Location is meant in a broad sense and refers also to parts of the human body. Hence, any concept vector and therefore any SNOMED concept can actually be shown on the virtual human body by considering the parts of the anatomy that are the most similar according to equation (3).

In the following, a mode of operation of the data summary unit 185 is described. The data summary unit 185 may in particular trigger highlighting some areas of interest on the virtual human body. These areas of interest may be either related to the medical history of a single patient or may correspond to some aggregated information gathered from a population of patients. Conceptually, a summary is an ordered list of anatomic parts/concepts with optionally a corresponding list of scores measuring how strongly the respective part should be highlighted. This summary can be computed from a list of concept vectors corresponding to a set of documents/electronic data records that has been selected by the user. Such selection may be, for example, related to the most recent medical entries or all documents containing the word stomach.

Let $F=\{f_1, \ldots, f_q\}$ be the q concept vectors corresponding to such a list. The summary unit 185 may rank the anatomic concepts according to the following similarity based algorithms, which perform data summary and can hence be denoted as summary algorithms. According to one similarity based algorithm each element of F may be considered as a vertex of the static similarity network $G_{EMR}$. These vertices can be for example, the first q elements of the network $v_1, \ldots, v_q$. Using the same propagation approach as in equation 5, the initial probability can be defined as $$p(0) = (\underbrace{1, \ldots, 1}_{q\text{times}}, 0, \ldots, 0).$$

The probability derived after a few propagations associates a score on each anatomic part. The rank of the anatomic parts can be derived from this score, wherein high scores are top ranked and are shown first on the human body. As this method is computationally intensive, it can be advantageously used for a summary on a single patient record.

According to another similarity based algorithm an average concept vector is computed as follows:

$$f_{avg} = \frac{1}{q}\sum_{i=1}^{q} f_i$$

Then the scores of each anatomic part are computed as its similarity from its corresponding concept vector to $f_{avg}$ according to equation (3). Then, the respective anatomic part is ranked according to this score, wherein the highest scored parts are put first.

Such approach is particularly well suited when the summary is about many electronic data records of many patients. It can also be extended to any way of computing a prototypical example of the set F such as the center of the smallest sphere containing all the elements of F.

The data summary unit 185 can be triggered by the user after selecting a set of documents or can be done automatically while the user types some text.

Figure 12:
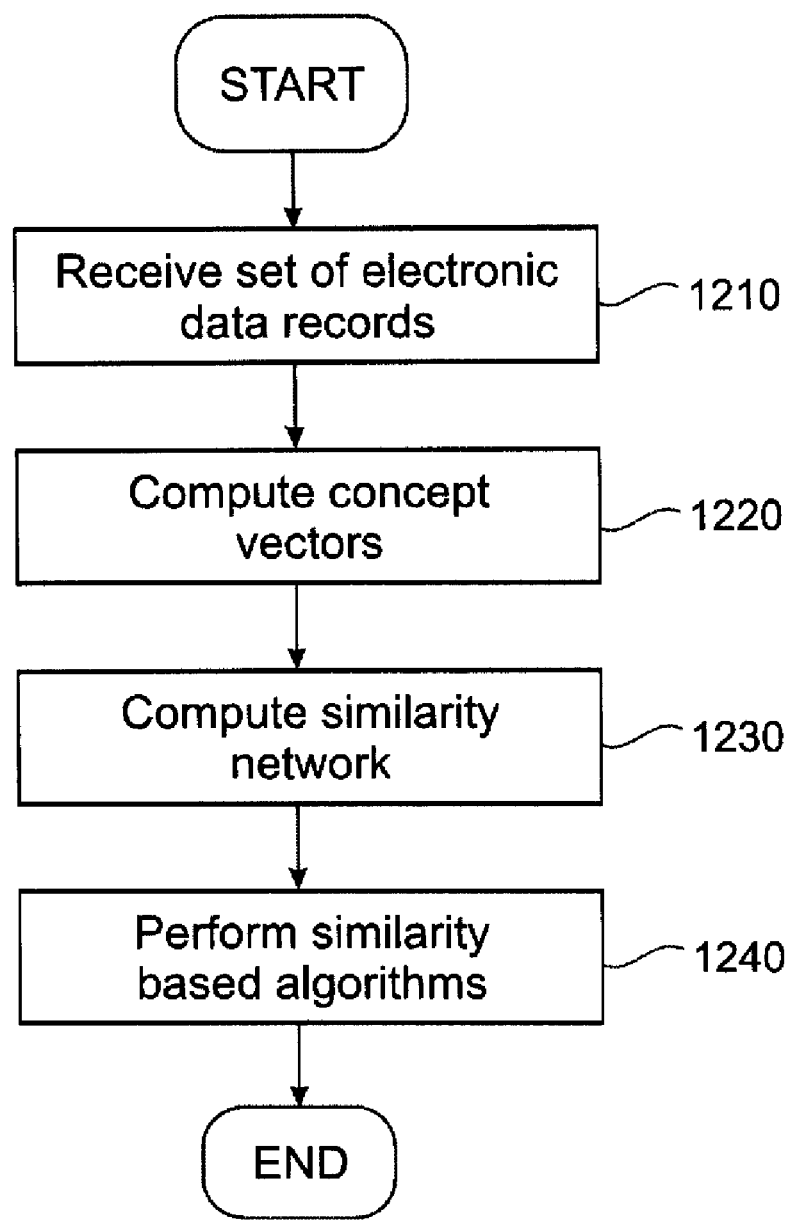
FIG. 12 shows a flow chart of a method for analyzing electronic data records.

FIG. 12 shows a flow chart of a method for analyzing electronic data records. The method can be performed by a system as described with reference to FIG. 1. Hence, in the following, also elements of FIG. 1 will be referenced.

In a step 1210 a set of electronic data records, for example, the first set 115 of electronic data records and the second set 125 of electronic data records, is received for performing an automated and computer-implemented analysis of the set of electronic data records.

In an annotation step 1220, the concept vectors 130 and 135 are computed for the set of electronic data records. The coordinates of the concept vectors 130 and 135 represent scores of the concepts in the respective electronic data record. The concepts are part of an ontology such as SNOMED.

In a similarity network computing step 1230, the similarity network 160 is computed by the similarity network unit 150. The similarity network unit 150 takes the concept vectors 130 and 135 as input.

In a similarity processing step 1240, predefined algorithms are performed over the similarity network 150 such as similarity based algorithms.

Exemplary embodiments of the invention have been described above purely by way of example and modifications of detail can be made within the scope of the invention.

Any disclosed embodiment may be combined with one or several of the other embodiments shown and/or described. This is also possible for one or more features of the embodiments.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries. Additionally, a description of an embodiment with several components in communication with each other does not imply that all such components are required. On the contrary a variety of optional components are described to illustrate the wide variety of possible embodiments.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article. The functionality and/or the features of a device may be alternatively embodied by one or more other devices which are not explicitly described as having such functionality/features. Thus, other embodiments need not include the device itself.

Computer program means or computer program in the present context mean any expression, in any language, code or notation, of a set of instructions intended to cause a system having an information processing capability to perform a particular function either directly or after either or both of the following a) conversion to another language, code or notation; b) reproduction in a different material form.

Any disclosed embodiment may be combined with one or several of the other embodiments shown and/or described. This is also possible for one or more features of the embodiments.

Any feature of one aspect of the invention may be applied to another aspect of the invention and vice versa.

What is claimed is:

1. A system for analyzing electronic data records, comprising:
    an annotation unit operable to receive a set of electronic data records and to compute concept vectors for the set of electronic data records wherein the coordinates of the concept vectors represent scores of the concepts in the respective electronic data record and wherein the concepts are part of an ontology;
    a similarity network unit operable to compute a similarity network by means of the concept vectors and by at least one relationship between the concepts of the ontology, the similarity network representing similarities between the electronic data records, wherein the vertices of the similarity network represent the electronic data records and the edges of the similarity network representing similarity values indicating a degree of similarity between the vertices; and
    a similarity processing unit operable to compute similarities between a first set of electronic data records and a second set of electronic data records.

2. The system of claim 1, further comprising a similarity processing unit operable to receive as input the similarity network and to perform predefined algorithms over the similarity network.

3. The system according to claim 2, wherein the similarity processing unit is operable to receive a query comprising at least one vertex of the similarity network and computing vertices of the similarity network that are similar to the query according to a predefined similarity criteria.

4. The system of claim 2, wherein the similarity network unit uses a kernel-based algorithm for computing the similarity values.

5. The system according to claim 1, wherein the similarity network unit uses a kernel-based algorithm for computing the similarity values.

6. The system of claim 5, wherein the similarity processing unit is operable to receive a query comprising at least one vertex of the similarity network and computing vertices of the similarity network that are similar to the query according to a predefined similarity criteria.

7. The system of claim 1, wherein the system is operable to analyze the first set of electronic data records and the second set of electronic data records, wherein the first set of electronic data records is a set of graphical electronic data records and the second set of electronic data records is a set of arbitrary electronic data records.

8. The system of claim 7, wherein the first set of electronic data records relate to a virtual model of an object, the object being a root concept of the ontology and wherein the second set of electronic data records represent data records of an individual of the root concept.

9. The system according to claim 8, wherein the object is a virtual model of a human body and the individuals are human patients.

10. The system of claim 7, comprising:
- a user interface for presenting a graphical representation of the first set of electronic data records, wherein the user interface comprises:
  - a navigation function for navigating over the graphical representation of the first set of electronic data records; and
  - a selection function for selecting parts of the graphical representation of the first set of electronic data records.

11. The system of claim 10, wherein the first set of electronic data records relates to a virtual model of a human body or a virtual model of an animal body and wherein the second set of electronic data records are electronic medical data records (EMR) of an individual patient.

12. The system of claim 7, wherein the first set of data records relates to a virtual model of an apparatus and the second set of data records relates to an individual apparatus.

13. The system of claim 7, wherein the second set of electronic data records are textual data records.

14. The system of claim 1, further comprising:
- an ontology database for storing data of the ontology;
- a graphical object database for storing graphical electronic data records of an object; and
- a database for storing electronic data folders, wherein each data folder comprises data records of an individual of the ontology.

15. The system according to claim 14, wherein the electronic data folders comprise electronic medical data records of a human patient.

16. The system of claim 1, wherein the system uses the Systematized Nomenclature of Medicine (SNOMED) as ontology.

17. The system of claim 1, further comprising at least one unit selected from the group consisting of:
- a data access unit for performing searches over the similarity network;
- a data entry unit operable to perform upon data entry a search for concepts of the ontology that are similar to the data entry and for presenting to the user one or more concepts that are similar to the data entry; and
- a data summary unit for computing a summary of one or more second sets of electronic data records, wherein the summary comprises a list of one or more graphical electronic data records being selected according to a predefined summary algorithm.

18. The system of claim 1, wherein the annotation unit comprises:
- a first annotation unit for computing concept vectors of electronic medical data records; and
- a second annotation unit for computing concept vectors of anatomic parts of a virtual human body.

19. The system of claim 1, wherein the similarity network unit is operable to compute a static similarity network representing similarities of the second set of electronic data records, compute a dynamic similarity network representing similarities between preselected graphical data records of the first set of electronic data records and dynamically selected graphical data records of the first set of electronic data records, wherein the dynamically selected graphical data records are dynamically selected dependent on user interaction, and linking the dynamic similarity network to the static similarity network.

20. A method for analyzing electronic data records, comprising the steps of:
- receiving a set of electronic data records;
- computing concept vectors for the set of electronic data records, wherein the coordinates of the concept vectors represent scores of the concepts in the respective electronic data record and wherein the concepts are part of an ontology;
- computing a similarity network by means of the concept vectors and by at least one relationship between the concepts of the ontology, the similarity network representing similarities between the electronic data records, wherein the vertices of the similarity network represent the electronic data records and the edges of the similarity network represent similarity values indicating a degree of similarity between the vertices;
- performing predefined algorithms over the similarity network; and
- computing similarities between a first set of electronic data records and a second set of electronic data records.

21. A computer program product having a computer usable program code configured to carry out instructions for analyzing electronic data records by a method comprising the steps of:
- receiving a set of electronic data records;
- computing concept vectors for the set of electronic data records, wherein the coordinates of the concept vectors represent scores of the concepts in the respective electronic data record and wherein the concepts are part of an ontology;
- computing a similarity network by means of the concept vectors and by at least one relationship between the concepts of the ontology, the similarity network representing similarities between the electronic data records, wherein the vertices of the similarity network represent the electronic data records and the edges of the similarity network represent similarity values indicating a degree of similarity between the vertices;
- performing predefined algorithms over the similarity network;
- computing similarities between a first set of electronic data records and a second set of electronic data records.

* * * * *